(12) United States Patent
Kawa

(10) Patent No.: US 6,479,712 B1
(45) Date of Patent: Nov. 12, 2002

(54) METHOD FOR PREPARING PERFLUOROCARBON-SUBSTITUTED METHANOLS

(75) Inventor: Hajimu Kawa, Austin, TX (US)

(73) Assignee: Exfluor Research Corporation, Round Rock, TX (US)

( * ) Notice: Subject to any disclaimer, the term of this patent is extended or adjusted under 35 U.S.C. 154(b) by 0 days.

(21) Appl. No.: 09/352,554

(22) Filed: Jul. 13, 1999

Related U.S. Application Data

(62) Division of application No. 08/932,763, filed on Sep. 17, 1997, now abandoned.
(60) Provisional application No. 60/026,475, filed on Sep. 18, 1996.

(51) Int. Cl.$^7$ .............................................. C07C 31/34
(52) U.S. Cl. ...................... 568/842; 568/812; 568/843; 568/831
(58) Field of Search ................................ 568/842, 843, 568/831, 812

(56) References Cited

U.S. PATENT DOCUMENTS

| | | | |
|---|---|---|---|
| 2,666,797 A | | 1/1954 | Husted et al. ............... 260/633 |
| 2,732,370 A | | 1/1956 | Codding .................... 260/91.1 |
| 2,911,444 A | * | 11/1959 | Barabauckas ............... 568/842 |
| 2,999,884 A | | 9/1961 | Weinmayr .................. 260/633 |
| 3,051,744 A | * | 8/1962 | Bowers ....................... 568/842 |
| 3,293,306 A | | 12/1966 | Le Bleu et al. ............. 260/615 |
| 3,478,116 A | * | 11/1969 | Smeltz ........................ 568/842 |
| 3,510,458 A | * | 5/1970 | Thayer ........................ 568/842 |
| 3,663,629 A | * | 5/1972 | Fischer ....................... 568/842 |
| 4,072,726 A | * | 2/1978 | Nychka ....................... 568/842 |
| 4,156,791 A | | 5/1979 | Childs ......................... 568/842 |
| 4,273,947 A | * | 6/1981 | Novotny ..................... 568/842 |
| 4,396,784 A | * | 8/1983 | Johnson ...................... 568/842 |
| 5,093,432 A | | 3/1992 | Bierschenk et al. ...... 525/331.6 |

FOREIGN PATENT DOCUMENTS

| | | |
|---|---|---|
| EP | 0079590 | 2/1986 |
| GB | 1213558 | 11/1970 |
| GB | 1224774 | 3/1971 |
| GB | 1262270 | 2/1972 |
| GB | 1319473 | 6/1973 |

OTHER PUBLICATIONS

Gambaretto et al. Preparazione di Alcuni Derivati Dell'acido Perfluorocicloesanoico' *Atti Dell'Tstituto Veneto di Scienze, Lettere ed Arti Classe di Scienze Matematiche e Naturali* 132:289–293 (1973–1974);.

Nguyen, T. et al. "Transformation de l'hexafluoropropéne en alcool trifluoroallylique prècurseur des alpha–fluoroacrylates" *Journal of Fluorine Chemistry* 74(2):273–277 (1995).

Vilenchik, Y. M. et al. *Zh. Vses. Khim. O–va.* 26(2):212–213.

Yagupol'skii, D.M. et al. "Polychloro and polyfluoro derivatives of 4–aryldifluoropyridine" *Journal of Organic Chemistry of the USSR, New York, U.S.* 28(4) part 2:606–609 (1992).

\* cited by examiner

*Primary Examiner*—Michael L. Shippen
(74) *Attorney, Agent, or Firm*—Lahive & Cockfield LLP; Giulio A. DeConti, Jr.

(57) ABSTRACT

Methods for producing perfluorocarbon monomethanols or dimethanols are disclosed. The methods of the invention can provide branched perfluorocarbon monomethanols or dimethanols with good purity and yields.

10 Claims, No Drawings

METHOD FOR PREPARING PERFLUOROCARBON-SUBSTITUTED METHANOLS

This application is a divisional of application Ser. No. 08/932,763 filed on Sep. 17, 1997, now abandoned. The contents of all of the aforementioned applications are incorporated herein by reference.

CROSS-REFERENCE TO RELATED APPLICATIONS

This applications claims benefit under 35 U.S.C. 119(e) to co-pending U.S. provisional application Serial No. 60/026,475, filed Sep. 18, 1996, the contents of which are hereby incorporated by reference.

BACKGROUND OF THE INVENTION

Perfluorocarbon monomethanols, especially perfluoroalkyl monomethanols represented by the general formula $CF_3(CF_2)_nCH_2OH$, are currently used in various applications. The perfluorocarbon methanols are acidic enough to chemically adhere to some surfaces to provide slick (low friction) and chemically inert properties. Polymers of acrylic and methacrylic esters derived from perfluorocarbon methanols are used for protective coatings which exhibit extremely low surface energy.

Among perfluorocarbon dimethanols, perfluoroalkylene dimethanols represented by the general formula $HOCH_2(CF_2)_nCH_2OH$, are important intermediates to synthesize various fluoro polymers which are useful as components of protective coatings and paints.

Many commercially available perfluoroalkyl monomethanols and perfluoroalkylene dimethanols possess are of the straight-chain perfluoroalkyl and perfluoroalkylene type. Only a few examples of branched perfluoroalkyl monomethanols and perfluoroalkylene dimethanols have been reported to date. Branched structures generally exhibit lower melting points than straight-chain structures. For example, 1H,1H-perfluoro-3,7-dimethyl-1-octanol (molecular formula: $C_9F_{19}CH_2OH$) is a free-flowing liquid at room temperature, while 1H,1H-perfluoro-1-decanol (which has the same molecular formula, but has a straight-chain perfluoroalkyl structure) has a melting point of 82–84° C. Since branched fluoroalkyl groups have multiple perfluoroalkyl groups, they may be able to cover surfaces more effectively than straight-chain perfluoroalkyl groups do. The way branched perfluoroalkylene dimethanols cover surfaces is very similar to that of fluoroalkyl acrylates such as perfluoro-1H,1H-octyl acrylate, $CF_3(CF_2)_6CH_2OCOCH=CH_2$. Fluoropolymers such as poly(perfluoro-1H,1H-octyl acrylate) contain relatively long perfluoroalkyl groups extending out from the polymer backbone, which provides a highly fluorinated surface. These polymers have been reported to give surfaces which have extremely low surface tensions (about 10 dyn/cm², Banks, R. E., "Organofluorine Chemicals and Their Industrial Application," John Wiley & Sons Inc., p 216, 1979), much lower than that of polytetrafluorethylene (Teflon) (about 18 dyn/cm²). It is believed that these surface properties are the result of a tight arrangement of the perfluoroalkyl groups. Though the polymer backbones (i.e., the polyacrylate polymers) do not contain any fluorine atoms, they exhibit excellent resistance against weathering, probably due to the protection provided by the perfluoroalkyl groups. Branched perfluorocarbon dimethanols are, therefore, expected to have many industrial applications.

When a primary perfluorocarboxylic acid ester is reduced, the alkoxy group (e.g., R in Scheme 1), such as a methoxy ($CH_3O$—) or ethoxy ($CH_3CH_2O$—) group, can function as a leaving group when the carbonyl group is attacked by hydride ion; this results in formation of a reactive aldehyde group. Then the intermediate aldehyde can be further reduced to give the alcohol as the final reduction product, as shown in Scheme 1, in which $R_f$ is a perfluorocarbon group.

Scheme 1

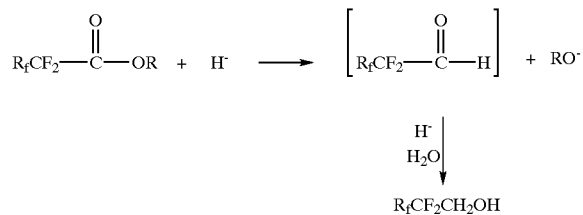

However, branched perfluoroalkyl groups, such as secondary and tertiary perfluoroalkyl moieties, sometimes act as pseudo halogens and therefore are good leaving groups. Because of this, it is very difficult to synthesize perfluoroalkyl methanols that have branching at the carbon atom next to the $CH_2OH$ group (this carbon atom can be referred to as the α-carbon atom). For example, it has been observed that, in contrast to primary perfluorocarboxylic acid esters, secondary perfluorocarboxylic acid esters which have branching at the carbon atom next to the carboxyl group (the α-carbon) may not yield the corresponding branched perfluoroalkyl methanols when the esters are chemically reduced under standard conditions for the reduction of esters, such as by treatment of the ester with lithium aluminum hydride (LAH) or sodium borohydride ($NaBH_4$). The products of attempted conventional reduction reactions can be quite complicated. It is believed that when there is a branch site at the carbon atom next to the carbonyl group, the secondary perfluoroalkyl group becomes a better leaving group than the alkoxy group because of the two strong electron withdrawing perfluoroalkyl groups. Thus, the secondary perfluoroalkyl group becomes a leaving group upon attack by hydride ion on the carboxylic ester functionality, producing a perfluoroalkyl anion and a formate ester, as shown in Scheme 2, in which R is an alkyl group and $R_f$ and $R'_f$ are perfluoroalkyl groups.

Scheme 2

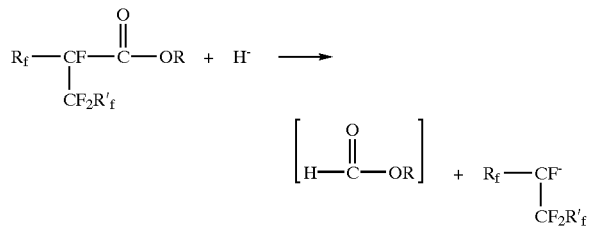

The formate ester may then be further reduced. The perfluoroalkyl anion can rapidly decompose into an olefin (Scheme 3), which can react further with the reducing reagent or with solvent to give a complicated product mixture.

Scheme 3

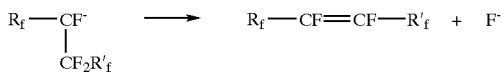

Possibly for the above-described reasons, there are few reports of syntheses of perfluorocyclohexylmethanol compounds by reduction of the corresponding esters. In one of the few successful preparations, (perfluorocyclohexyl) methanol was successfully prepared by the reduction of perfluorocyclohexanecarboxylic acid fluoride with sodium borohydride (Scheme 4; the "F" in the cycloalkyl ring in Scheme 4 indicates that the cyclohexyl ring is perfluorinated) (Gambaretto, Giampaolo, et al. *Att. Ist. Veneto Sci., Lett. Arti. Cl. Sci. Mat. Nat.* 1973, 132, 289–93; C. A. 83, 163685e). However, this procedure may require the synthesis of the corresponding carboxylic acid, followed by conversion to the acid halide (e.g., acid fluoride. Such a two-step procedure can be cumbersome and inefficient.

Scheme 4

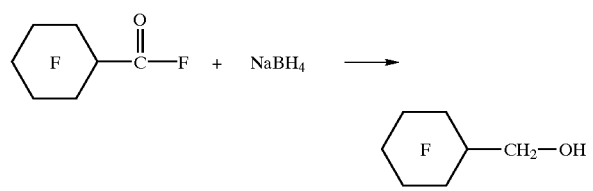

Similarly, perfluoropolyether alkyl methanols were synthesized as shown in Scheme 5 (Vilenchik, Ya. M.; Lekentseva, G. I. 'neifel'd, P. G. and Pospelova, N. B., Zh. Vses. Khim. O-va. 1981, 26(2), 212–3.; C. A. 95, 96946y).

Scheme 5

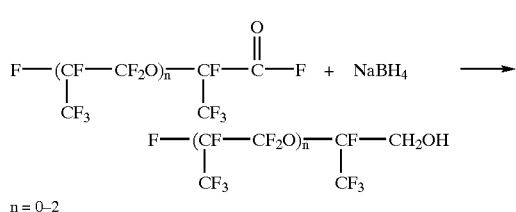

n = 0–2

Certain perfluoropolyethers (e.g., as shown in Scheme 5) have perfluoroalkoxy groups directly attached to the carbon atom next to the carbonyl group (the α-carbon). Perfluoroalkoxy groups generally do not have as strong an electron withdrawing effect as perfluoroalkyl groups, possibly because of the electron rich oxygen atom, and may therefore make a perfluoroalkylene group which is substituted with the perfluoroalkoxy moiety a poorer leaving group than a corresponding perfluoroalkyl group. Thus, while poor results are often obtained upon reductive treatment of branched (perfluoralkyl) carboxylic methyl esters (e.g., Scheme 2, in which R is a methyl group, see supra), perfluoropolyether methanols can be prepared by the reduction of alkyl esters (e.g., methyl esters, as shown in Scheme 6) (Tamaru, Sinji, European Patent Application No. EP 79,590).

Scheme 6

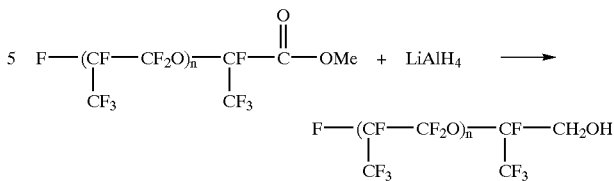

SUMMARY OF THE INVENTION

The present invention relates to methods for producing perfluorocarbon-substituted methanols, including straight- and branched-chain perfluoralkylmethanols, straight- and branched-chain perfluoroalkylene dimethanols, and perfluorocycloalkyl methanols. The method also provides novel perfluorocarbon-substituted methanols, including straight- and branched-chain perfluoralkylmethanols, straight- and branched-chain perfluoroalkylene dimethanols, and perfluorocycloalkyl methanools. The invention further provides perfluorocarbon-substituted methanols prepared according to the methods of the invention.

In one embodiment, the invention provides a method for preparing a perfluorocarbon methanol. The method includes reacting a perfluorocarbon ester of a perfluorocarbon carboxylic acid with a reducing reagent under reducing conditions, such that a perfluorocarbon methanol is prepared. The perfluorocarbon ester of a perfluorocarbon carboxylic acid can be represented by the formula $R_f$—C(O)OR″$_f$, in which $R_f$ and R″$_f$ are each independently a substituted or unsubstituted perfluoroalkyl group. In certain embodiments, R″$_f$ can be —CF$_2$R′″$_f$, in which R′″$_f$ is a perfluoroalkyl group. In some embodiments, the perfluorocarbon methanol can be represented by the formula $R_f$—CF(R′$_f$)—CH$_2$OH, in which $R_f$ and R′$_f$ are each independently perfluoroalkyl. In certain embodiments, the perfluorocarbon ester of a perfluorocarbon carboxylic acid is a lactone. In certain embodiments, the reducing reagent comprises a metal hydride, while in other embodiments, the reducing reagent comprises a hydrogen source and a catalyst, such as a noble metal catalyst selected from the group consisting of a platinum catalyst and a palladium catalyst.

In another aspect, the invention provides a method for preparing a compound represented by the formula $R_f$—CH$_2$OH, in which $R_f$ is a moiety selected from the group consisting of perfluoroaliphatic moieties and perfluoroaryl moieties. The method includes reacting a perfluorocarbon ester of a perfluorocarbon carboxylic acid represented by the formula $R_f$—COOR″$_f$, in which R″$_f$ is perfluoroaliphatic or perfluoroaromatic, with a reducing reagent under reducing conditions, such that a compound represented by the formula $R_f$—CH$_2$OH is prepared.

In another embodiment, the invention provides a perfluorocarbon methanol compound having a hydroxymethyl group and an carbon atom attached to the hydroxymethyl group, wherein the carbon atom attached to the hydroxymethyl group is substituted with at least one perfluorocarbon moiety, with the proviso that the compound is not (perfluorocyclohexyl)methanol and with the further proviso that the carbon atom attached to the hydroxymethyl group is not substituted with a perfluoroalkoxy moiety.

In another aspect, the invention provides a compound selected from the group consisting of perfluoro-1H,1H-2-hexyldecanol, 2-fluoro-2-perfluorooctyl-1,3-propanediol, 2-fluoro-2-perfluorobutyl-1,3-propanediol, perfluoro 1H,1H,4H-undecane 1,4-diol, and perfluoro 1H,1H,5H-dodecan-1,4-diol.

In another embodiment, the invention provides a perfluoro 1H,1H,nH-alkyl-1,n-diol, in which the alkyl moiety includes from 3 to 15 carbon atoms, and n is an integer from 3 to 5.

In another aspect, the invention provides a perfluoroalkyl methanol compound represented by the formula HOCH($R_f$)—$R'_f$—$CH_2OH$, wherein $R'_f$ is a substituted or unsubstituted perfluorocarbon moiety and $R_f$ is a substituted or unsubstituted perfluorocarbon moiety. $R'_f$ can be an unsubstituted or substituted divalent, perfluorinated, alkyl or alkenyl organic radical having one to twenty fully fluorinated carbon atoms, which radical can be interrupted by divalent oxygen or sulfur atoms, and $R_f$ can be a substituted or unsubstituted perfluoroalkyl moiety.

In another embodiment, the method provides a perfluorocarbon dimethanol compound represented by the formula $R_f$—C($R'_f$)($CH_2OH$)$_2$, wherein $R_f$ and $R'_f$ are each independently a substituted or unsubstituted perfluorocarbon moiety. $R_f$ and $R'_f$ can each independently be an unsubstituted or substituted monovalent, perfluorinated, alkyl or alkenyl organic radical having one to twenty fully fluorinated carbon atoms, which radical can be interrupted by divalent oxygen or sulfur atoms.

In still another embodiment, the invention provides a perfluoroalkyl methanol prepared by the methods of the invention.

DETAILED DESCRIPTION OF THE INVENTION

For convenience, certain terms used throughout the specification and claims are defined.

The term "perfluorocarbon", as used herein, refers to a moiety which includes a carbon backbone which is substituted with one or more fluorine atoms, and which preferably does not include any covalent bonds between carbon and hydrogen. Exemplary perfluorocarbons include perfluorinated monovalent aliphatic groups (including perfluoroalkyls, alkenyls, and alkynyls) and perfluorinated aryl groups (such as phenyl, pyridinyl, and the like), as well as divalent groups such as perfluoroalkylene, perfluoroalkenylene, perfluoroalkynylene, and perfluoroarylene (e.g., 1,4-phenylene). A preferred monovalent perfluorocarbon is a perfluoroalkyl, while a preferred divalent perfluorocarbon is perfluoroalkylene. A perfluorocarbon moiety such as a perfluoroalkyl can often be prepared from a corresponding non-fluorinated moiety, e.g., a hydrocarbyl moiety, by perfluorination, e.g., according to reported methods for perfluorination. It will be appreciated, however, that perfluorination may destroy certain functionalities, such as olefins, and perfluorination of, e.g., alkenyls, may be difficult. Perfluorocarbons can be straight or branched-chain, or cyclic, and can be unsubstituted or substituted as described hereinafter.

The term "perfluorocarbon-substituted methanol" is a methanol having at least one hydrogen atom replaced by a perfluorocarbon moiety. Thus, a perfluorocarbon-substituted methanol can be represented by the formula $R_f$—$CH_2OH$, in which $R_f$ is a perfluorocarbon moiety (preferably a perfluoroalkyl moiety). It will be appreciated that, in certain embodiments, the hydrogen atoms of a perfluorocarbon-substituted methanol (i.e., in the moiety —$CH_2OH$) can be deuterium or tritium atoms. Preferred perfluorocarbon-substituted methanols can be represented by the formula

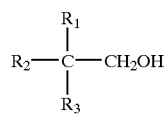

in which $R_1$, $R_2$, and $R_3$ are each independently selected from the group consisting of fluorine, straight- or branched-chain perfluoro aliphatic moieties (including substituted or unsubstituted perfluoroalkyls, perfluoroalkenyls, and perfluoroalkynyls) and perfluoroaryls. In preferred embodiments, at least one of $R_1$, $R_2$, and $R_3$ is a perfluoroalkyl group. In preferred embodiments, at least one of $R_1$, $R_2$, and $R_3$ is not a fluorine atom; in particularly preferred embodiments, at least two of $R_1$, $R_2$, and $R_3$ are not fluorine atoms; in this instance, the perfluorocarbon-substituted methanol is branched at the α-carbon (the carbon atom to which $R_1$, $R_2$, and $R_3$ are attached). In embodiments in which at least one of $R_1$, $R_2$, and $R_3$ is a substituted perfluoroalkyl group, a preferred substituent of the substituted perfluoroalkyl is a perfluoroalkoxy group.

The term "perfluorocarbon dimethanol" refers to a compound having a perfluorocarbon moiety which is substituted with two hydroxymethyl ($CH_2OH$) groups. Thus, a perfluorocarbon dimethanol can be represented by the formula $HOCH_2$—$R_f$—$CH_2OH$, in which $R_f$ is a straight- or branched-chain perfluoroalkylene, perfluoroalkenylene, perfluoroalkynylene, or perfluoroarylene group (such as phenylene, pyridinylene, naphthalenylene (i.e., —$C_{10}F_6$—), and the like); perfluoroaliphatic groups (particularly perfluoroalkylene groups) are preferred.

The term "perfluorocarbon polymethanol" refers to a compound having a perfluorocarbon moiety substituted with at least three hydroxymethyl ($CH_2OH$) groups.

The language "perfluoroalkyl ester of a perfluoroalkyl carboxylic acid" refers to a compound having the formula $R_f$—C(O)O$R''_f$, in which $R_f$ and $R''_f$ are perfluoroalkyl groups (which may be the same or different, branched or straight, and substituted or unsubstituted); or $R_f$ and $R''_f$, taken together with the carboxyl group to which they are attached, form a cyclic ester (a lactone). In another preferred embodiment, $R''_f$ is a primary perfluoroalkyl group, i.e., —CF$_2$R'''$_f$, in which R'''$_f$ is a perfluoroalkyl group. A "perfluoroalkyl carboxylic acid" can be represented by the formula $R_f$—C(O)OH, $R_f$ is a perfluoroalkyl group (which may be branched or straight, and substituted or unsubstituted). It will be appreciated that the term "perfluoroalkyl ester of a perfluoroalkyl carboxylic acid" is employed for convenience and is not intended to suggest that such an ester is necessarily prepared by esterification of a perfluoroalkyl carboxylic acid. Indeed, in certain embodiments, a "perfluoroalkyl ester of a perfluoroalkyl carboxylic acid" can be prepared by perfluorination of an alkyl ester (of a carboxylic acid) (see, e.g., the Examples, infra). The term "perfluorocarbon ester of a perfluorocarbon ester of a carboxylic acid" refers to a compound having the formula $R_f$—C(O)O$R''_f$, in which $R_f$ and $R''_f$ are perfluorocarbon groups (which may be the same or different, branched or straight, and substituted or unsubstituted); or $R_f$ and $R''_f$, taken together with the carboxyl group to which they are attached, form a cyclic ester (a lactone).

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Preferred cycloalkyls have from 4–10 carbon atoms in their ring structure, and more preferably have 5, 6 or 7 carbons in the ring structure. A perfluoroalkyl group is an alkyl group in which all C—H bonds are replaced by C—F bonds.

Moreover, the term "alkyl" as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkoxyl, cyano, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)). A perfluoroalkyl moiety can be substituted with substituents as described for alkyl groups, although such substituents are preferably perfluorinated. Exemplary perfluoroalkyl groups include trifluoromethyl, pentafluoroethyl, heptafluoroisopropyl, 2-trifluoromethoxy perfluoropentyl, perfluorocyclopentyl, and the like.

The term "aryl" as used herein includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such substituents as described above, as for example, halogen, hydroxyl, alkyl, alkoxy, cyano, azido, heterocylyl, alkyl, aralkyl, or an aromatic or heteroaromatic moiety. Aryl groups can also be fused or bridged with alicyclic or heterocyclic rings which are not aromatic so as to form a polycycle (e.g., tetralin). A perfluoroaryl group can be substituted with substituents as described for aryl groups, athough such substituents are preferably perfluorinated.

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms, in its backbone structure. Likewise, "lower alkenyl" and "lower alkynyl" have similar chain lengths. Preferred alkyl groups are lower alkyls.

The term "reducing agent" is art-recognized and is intended to include any agents which are capable of converting a carbonyl group into the corresponding alcohol. A variety of reducing agents are well known to the ordinarily skilled artisan (for example, see, e.g., R. Larock, "Comprehensive Organic Transformations", VCH Publishers, Inc., 1989). Examples of preferred reducing agents include sodium borohydride, lithium borohydride, lithium aluminum hydride, and diborane. Catalytic hydrogenation (e.g., with a metal catalyst such as palladium (e.g., palladium on carbon or tetrakis(triphenylphosphine)palladium(0)), platinum (e.g., platinum on carbon), or rhodium (e.g., tetrakis (triphenylphosphine)rhodium(I) chloride), or the like, can also be employed with a suitable hydrogen donor source.

Examples of hydrogen sources include hydrogen gas (e.g., a catalytic reduction performed under an atmosphere of hydrogen gas), cyclohexene, and the like.

I. Methods

In one aspect, the invention relates to methods for preparing perfluorocarbon-substituted methanols. The methods of invention allow synthesis of straight- or branched-chain perfluorocarbon-substituted methanols, dimethanols, and polymethanols, which can be difficult to prepare by conventional methods. The methods of the invention are also applicable to the synthesis of branched perfluorocarbon dimethanols. Such branched fluoro compounds are believed to possess improved surface-modifying properties, such as lowered surface energy, enhanced chemical stability, increased UV stability and so on, compared to straight-chain fluoro compounds, due to the ability of branched perfluoro compounds to cover surfaces more effectively than straight-chain compounds.

According to the present invention, there is provided a method of producing straight- or branched-chain perfluorocarbon monomethanols or dimethranols (or, in certain cases, polymethanols). The method involves the reduction of perfluorinated carboxylic acid esters or diesters (or greater numbers of ester moieties) to provide the corresponding perfluorocarbon methanols. The methods of the invention provide access to compounds which have heretofore been difficult to obtain in good yield. Moreover, in preferred embodiments, the methods of the invention provide the desired perfluorocarbon methanol compounds in a single step from readily prepared stable starting materials, often in high yield. Thus, the invention provides a simple, rapid, relatively inexpensive and quite general method for the preparation of a variety of perfluorocarbon methanol compounds.

The methods of the invention are based, at least in part, on the understanding that the leaving group (such as Y in Scheme 7) of a perfluorocarbon carboxylic acid derivative I should, in general, be a better leaving group than the secondary or tertiary perfluoroalkyl group in order to successfully synthesize alpha branched perfluoroalkyl methanols II as illustrated in Scheme 7.

Scheme 7

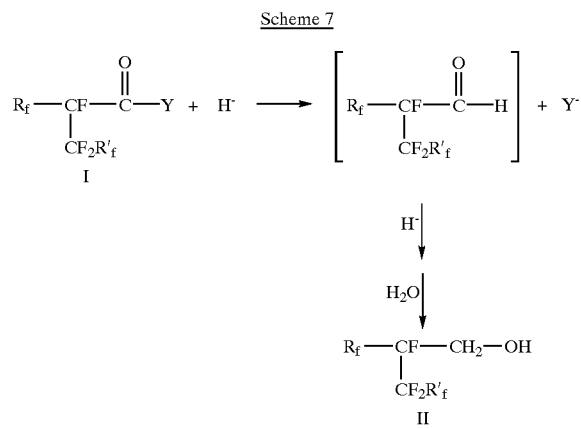

It has now been found that reduction of compounds such as compound I, in which Y is a perfluorocarbon group, such as a perfluoroalkoxy or perfluoroaryloxy moiety (e.g., $R''_fO$—, in which $R''_f$ is a perfluoroalkyl or perfluoroaryl group, more preferably a perfluoroalkyl group) can be accomplished smoothly and in good to excellent yield under simple conditions. Since perfluoroalkoxy groups are generally better leaving groups than perfluoroalkyl groups, the reduction reaction proceeded smoothly to yield perfluorocarbon monomethanols or dimethanols even when there was a branch site at the carbon atom next to the carbonyl group.

An exemplary reaction scheme for the reduction of a perfluoroalkyl ester of a perfluoroalkyl carboxylic acid is shown in Scheme 8.

carbonyl fluoride, and reduction, is methanol. If Y in Scheme 7 is a tertiary group (i.e., $-OC(R_{1f})(R_{2f})(R_{3f})$, in which $R_{1f}$, $R_{2f}$ and $R_{3f}$ are each perfluorocarbon moieties, the product after ester cleavage, is $HOC(R_{1f})(R_{2f})(R_{3f})$. Thus, the leaving group moiety can be selected to provide a desired product or avoid undesired products.

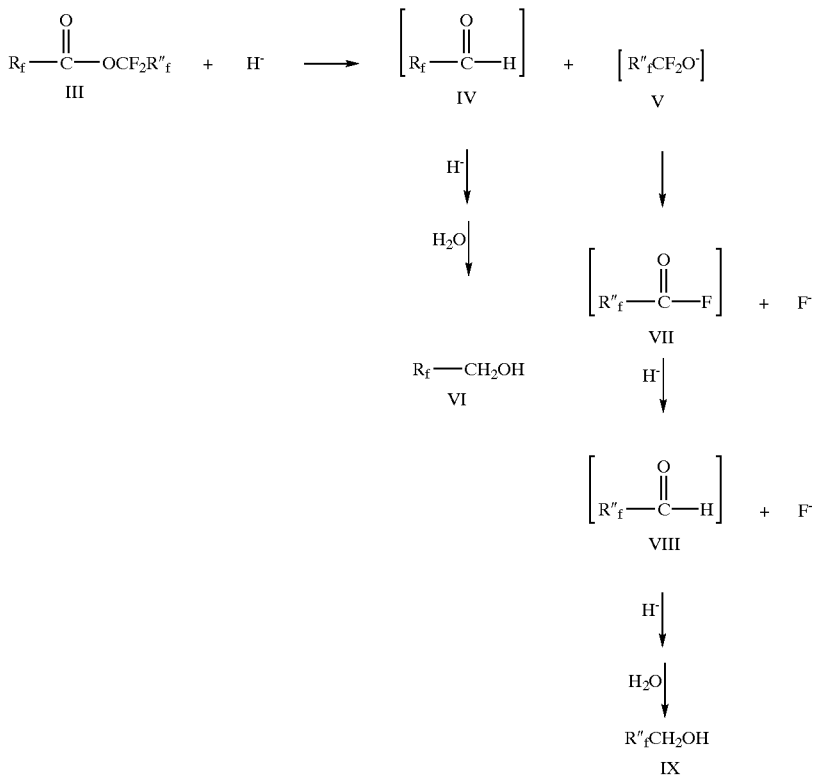

Scheme 8

Without wishing to be bound by theory, it is believed that initial hydride attack at the carbonyl group of III (in which $R_f$ and $R''_f$ are both perfluorocarbon (e.g., perfluoroalkyl) moieties, which can be the same or different) initially yields a perfluoroalkanal (aldehyde) IV and a perfluoroalkoxide ion V. The perfluoroalkanal IV is further reduced to the perfluorocarbon (e.g., perfluoroalkyl) methanol VI. Perfluoroalkoxide ion V, on the other hand, immediately decomposes into perfluorocarboxylic acid fluoride VII and fluoride ion. Since the fluoride group is a very good leaving group, as mentioned supra, the perfluorocarboxylic acid fluoride VII can be reduced (via perfluoroaldehyde VIII) to another perfluoroalkyl methanol IX even if the group $R''_f$ is a secondary or tertiary perfluoroalkyl group.

In Scheme 8, the leaving group (corresponding to Y in Scheme 7) has the formula $-OCF_2R''_f$. The resultant fluoroalkoxide decomposes to produce a perfluorocarbon methanol. However, it will be appreciated that other perfluorinated moieties can serve as leaving groups, and other products can be expected. For example, if Y in Scheme 7 has the formula $-OCF(R_{1f})(R_{2f})$, in which $R_{1f}$ and $R_{2f}$ are each perfluorocarbon moieties, decomposition of the released fluoroalkoxide will yield a ketone, which can be reduced under the reaction condition to yield a compound of the formula $R_{1f}CH(OH)-R_{2f}$. If Y in Scheme 7 is a trifluoromethyl group, the product after ester cleavage, decomposition to It can be seen from Scheme 8 that the reduction of one mole of perfluorinated ester gives two moles of perfluoroalkyl methanols (one mole each of $R_fCH_2OH$ and $R''_fCH_2OH$). It will be appreciated that one mole of a compound of formula III, in which $R_f$ and $R''_f$ are identical, can be reduced to provide two moles of the desired product $R_fCH_2OH$. This represents a highly efficient synthesis with little wasted material. It will also be appreciated that reduction of a perfluoroester compound having the formula $R_fC(O)OCF_2R''_f$ can provide the same products after reduction as the compound $R''_fC(O)OCF_2R_f$. For example, reduction of perfluoro(ethyl 2-methylpropionate) (formula $CF_3CF(CF_3)C(O)OCF_2CF_3$) provides the same products as does reduction of perfluoro(2-methylpropyl acetate) (formula $CF_3C(O)OCF_2CF(CF_3)CF_3$); in each case, perfluroisopropylmethanol (perfluoro 1H,1H-sec-butanol) and trifluoromethylmethanol (2,2,2-trifluoroethanol). Thus, it is often possible to select from two perfluorinated esters as starting materials for reduction to provide the desired product or products. The more readily available, or less costly, starting material can then be employed.

The methods of the invention also provide access to a wide variety of straight- and branched-chain perfluoroalkylene or perfluoroarylene dimethanols. For example, perfluoroalkylene or perfluoroarylene dimethanols can be prepared by the hydride reduction of perfluorinated esters. In one embodiment, a perfluorinated alkylene or arylene diester is reduced to provide a perfluoroalkylene or arylene dimethanol. Thus, for example, in one embodiment, reduction of a compound represented by the formula R"$_f$C(O)OCF$_2$R$_f$CF$_2$OC(O)R"$_f$, in which R$_f$ is a perfluoroalkylene or perfluorarylene moiety, and each R"$_f$ is a perfluorocarbon group which may be the same or different (e.g., a perfluoralkyl or perfluoroaryl group), provides a perfluorodimethanol of the formula HOCH$_2$R$_f$CH$_2$OH along with two equivalents of R"$_f$CH$_2$OH). The starting material can be readily prepared from a diol of the formula HOCH$_2$RCH$_2$OH (a variety of which are commercially available) by esterification under standard conditions with a carboxylic acid of the formula R"COOH (or a derivative thereof), to yield a diester of the form R"C(O)OCH$_2$RCH$_2$OC(O)R" (R and R" are the non-fluorinated analogs of R$_f$ and R"$_f$). Note that the non-fluorinated diol HOCH$_2$RCH$_2$OH and non-fluorinated carboxylic acid R"COOH can be employed instead of the fluorinated (and likely more expensive) HOCF$_2$R$_f$CF$_2$OH and R"$_f$COOH, although the fluorinated compounds could be used if desired. The diester R"C(O)OCH$_2$RCH$_2$OC(O)R" can then be perfluorinated by methods known in the art (e.g., see infra) to provide the diester R"$_f$C(O)OCF$_2$R$_f$CF$_2$OC(O)R"$_f$ for reduction.

In another embodiment, reduction of a compound represented by the formula R"$_f$CF$_2$OC(O)R$_f$C(O)OCF$_2$R"$_f$, in which R$_f$ is a perfluoroalkylene or perfluorarylene moiety and each R"$_f$ is a perfluoroaliphatic or perfluoroaryl moiety, provides a perfluorodimethanol of the formula HOCH$_2$R$_f$CH$_2$OH (along with two equivalents of R"$_f$CH$_2$OH). It will be appreciated that the products of reduction are the same as in the previous instance. The perfluoro diester R"$_f$CF$_2$OC(O)R$_f$C(O)OCF$_2$R"$_f$ can be prepared by esterification of a diacid HOC(O)RC(O)OH with a suitable alcohol R"CH$_2$OH (R and R" are the non-fluorinated analogs of R$_f$ and R"$_f$), to provide a diester, followed by perfluorination of the diester to produce the required perfluorinated diester.

The methods of the invention also contemplate reduction of perfluoroaliphatic lactones (cyclic esters) to produce diols. For example, reduction of a gamma lactone can provide a perfluoroalkyl 1,4-butane diol, as depicted in Scheme 9, below.

Scheme 9

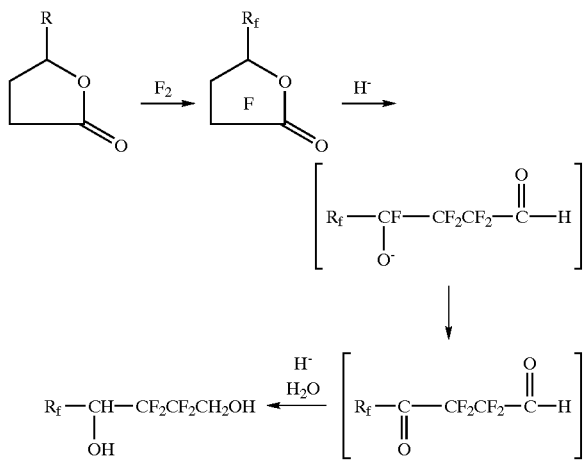

As depicted in Scheme 9, perfluoroalkyl-substituted 1,4-butanediols can be synthesized conveniently from commercially available gamma lactones (see Example 6, infra). Perfluorination of the gamma lactone provides a perfluorinated lactone (R$_f$ is a perfluorinated substituent) which is reduced to provide a ring-opened intermediate fluoroalkoxide-aldehyde. The fluoroalkoxide decomposes to a ketone, and both the ketone and ester functionalities are reduced to provide a perfluoro 1H,1H,4H-alkyl 1,4-diol. Fluorinated 1,5-pentanediols can be similarly prepared from delta lactones (see Example 7, infra). Other unsubstituted or substituted lactones, having from 4 to 16 atoms in the ring, more preferably 4 to 9 atoms in the ring, still more preferably from 5 to 7 atoms in the ring, can be employed. Thus, the invention provides a simple route to perfluoro 1H,1H, nH-alkyl 1,n-diols, in which n is an integer from 3 to 15, more preferably 3 to 8, and more preferably 4 to 6 atoms in the ring.

As described above, the present invention provides a straightforward method to synthesize a wide variety of branched perfluorocarbon monomethanols and dimethanols. The starting perfluorinated carboxylic acid esters and diesters can be prepared directly from the corresponding hydrocarbon esters by liquid phase fluorination such as the one described by Bierschenk et al (U.S. Pat. No. 5,093,432).

The reactions of the present invention may be performed under a wide range of conditions, though it will be understood that the solvents and temperature ranges recited herein are not limitative and only correspond to a preferred mode of the process of the invention. The reaction conditions (temperature, choice of solvent, choice of reducing agent or catalyst, order of addition of reagents, etc.) can be selected according to factors well known to one of ordinary skill in the art. In preferred embodiments, the particular reducing agent employed can be selected to reduce a carboxylic ester functionality of a perfluorinated ester, while minimizing concomitant reduction of other functional groups (if any) present in the starting materials or desired products. For example, if the starting ester and desired product include an olefinic (double bond) functionality, it is preferred to select a reducing agent, and other reaction conditions, such that reduction of the double bond is minimized.

In certain preferred embodiments, a reduction reaction is carried out generally by adding a perfluorinated ester to a mixture containing a solvent and a reducing agent. The perfluorinated ester can be added directly (neat) to the reaction vessel, or after being diluted with a diluent, e.g., for ease of handling. Various diluents can be employed. Suitable diluents include perfluorinated hydrocarbons, chlorofluorocarbons, bromofluorocarbons and perfluoroethers. One preferred diluent is Halocarbon oil 0.8™ (an oligomer of chlorotrifluoroethylene) (available from Halocarbon Products Corp.).

Reduction reactions according to the invention are preferably conducted in a fluid medium, e.g., in suspension or solution in a solvent. A variety of solvents are suitable; preferred solvents include ethers such as diethyl ether, tetrahydrofuran, dioxane and diglyme. In general, a solvent should be selected to avoid unwanted reaction with the starting ester or the reducing agent. For example, a protic solvent such as an alcohol should generally not be employed in conjunction with a highly reactive reducing agent such as lithium aluminum hydride. A suitable solvent can be selected by one of ordinary skill in the art using no more than routine experimentation in light of the teachings herein.

In general, reactions according to the invention can be performed over a range of temperatures from about −80° C. up to the boiling point of the solvent or solvent mixture employed. In general, reactions will be usually be run at temperatures in the range of −78° C. to 150° C., more preferably in the range −20° C. to 100° C. When sodium borohydride is used as a reducing agent, reaction temperatures preferably range between about −20° C. and 100° C., and more preferably between about 10° C. and 60° C.

In certain embodiments it is preferable to perform the reactions under an inert atmosphere of a gas such as nitrogen or argon.

In certain instances, the reactions of the invention can produce fluoride ion as a byproduct. Fluoride ion can be destructive to glass vessels, so in certain embodiments it is advantageous to employ plastic or plastic-coated reaction vessels to avoid such damage.

II. Compounds

In another aspect, the invention provides novel perfluorocarbon compounds. The invention provides compounds having a variety of structures, including perfluorocarbon methanols and dimethanols, in which the fluorocarbon moiety can be cyclic, straight, or branched. Perfluorocarbon methanols are well known for surface modification. It has been reported that certain perfluorocarbon diols are useful for preparation of water-repellent protective materials (see, e.g., U.S. Pat. Nos. 3,935,277, 3,968,066, 4,046,944, 4,054, 592, 4,098,742, 4,946,992, 5,663,273), including polyurethanes.

In one embodiment, the invention provides a perfluorocarbon methanol compound having a hydroxymethyl group and an carbon atom attached to the hydroxymethyl group, wherein the carbon atom attached to the hydroxymethyl group is substituted with at least one perfluorocarbon moiety, with the proviso that the compound is not (perfluorocyclohexyl)methanol and with the further proviso that the carbon atom attached to the hydroxymethyl group is not substituted with a perfluoroalkoxy moiety. Thus, in one embodiment, the compound can be represented by the formula

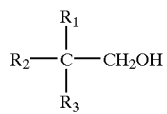

in which $R_1$ and $R_2$ are each independently selected from the group consisting of straight- or branched-chain perfluoro aliphatic moieties (including substituted or unsubstituted perfluoroalkyls, perfluoroalkenyls, and perfluoroalkynyls) and perfluoroaryls, and $R_3$ is selected from the group consisting of fluorine, straight- or branched-chain perfluoro aliphatic moieties (including substituted or unsubstituted perfluoroalkyls, perfluoroalkenyls, and perfluoroalkynyls) and perfluoroaryls; with the proviso that the compound is not (perfluorocyclohexyl)methanol. In this embodiment, the perfluorocarbon-substituted methanol is branched at the α-carbon (the carbon atom to which $R_1$, $R_2$, and $R_3$ are attached). In preferred embodiments, at least one of $R_1$ and $R_2$ is a perfluoralkyl group. In embodiments in which at least one of $R_1$, $R_2$, and $R_3$ is a substituted perfluoroalkyl group, a preferred substituent of the substituted perfluoroalkyl is a perfluoroalkoxy group.

In another embodiment, the invention provides the compounds perfluoro-1H,1H-2-hexyldecanol, 2-fluoro-2-perfluorooctyl-1,3-propanediol, 2-fluoro-2-perfluorobutyl-1,3-propanediol, perfluoro1H,1H,4H-undecane 1,4-diol, and perfluoro 1H,1H,5H-dodecan-1,4-diol. The synthesis of these compounds is detailed in the Examples, infra.

In another embodiment, the invention provides perfluoro 1H,1H,nH-alkyl 1,n-diols, in which the perfluoralkyl moiety is straight—or branched-chain, substituted or unsubstituted. The perfluoralkyl chain preferably includes from 3 to 15 carbon atoms, and n is an integer from 3 to 15, more preferably 3 to 8, and more preferably 4 to 6 atoms in the ring. As described above, the perfluoro 1H,1H,nH-alkyl 1,n-diols can be prepared by reduction of perfluoralkyl lactones.

In another embodiment, the invention provides a perfluorocarbon methanol compound represented by the formula $HOCH(R_f)$—$R'_f$—$CH_2OH$, wherein $R'_f$ is a substituted or unsubstituted perfluorocarbon moiety and $R_f$ is a substituted or unsubstituted perfluorocarbon moiety. In preferred embodiments, $R'_f$ is an unsubstituted or substituted divalent, perfluorinated, alkyl or alkenyl straight, branched or cyclic organic radical having one to twenty (more preferably one to ten) fully fluorinated carbon atoms, which radical can be interrupted by divalent oxygen or sulfur atoms. In certain embodiments, $R_f$ is a substituted or unsubstituted perfluoroalkyl moiety having from one to twenty (more preferably one to ten) carrbon atoms in the perfluoralkyl chain.

In yet another embodiment, the invention provides a perfluorocarbon dimethanol compound represented by the formula $R_f$—$C(R'_f)(CH_2OH)_2$, wherein $R_f$ and $R'_f$ are each independently a substituted or unsubstituted perfluorocarbon moiety. In certain embodiments, $R_f$ and $R'_f$ are each independently an unsubstituted or substituted monovalent, perfluorinated, alkyl or alkenyl organic radical having one to twenty fully fluorinated carbon atoms, which radical can be interrupted by divalent oxygen or sulfur atoms.

In still another embodiment, the invention provides perfluorcarbon compounds prepared by the any of the methods of the invention as described herein The present invention is further illustrated by the following non-limiting examples.

EXAMPLE 1

Attempted Reduction of Methyl Perfluoro(2-Hexyldecanoate)

In this example, the reduction of a methyl ester of a branched perfluoroalkanoic carboxylic ester was attempted.

Methyl perfluoro(2-hexyl decanoate) (formula $CF_3(CF_2)_7CF((CF_2)_5CF_3)COOMe$) was prepared by treating perfluoro (2-hexyldecyl acetate) ($CF_3(CF_2)_7CF((CF_2)_5CF_3)CF_2OC(O)CF_3$) with methanol in quantitative yield. Methyl perfluoro(2-hexyl decanoate) 88.0 g (0.106 mole) was added to a mixture of sodium borohydride 10.0 g (0.263 mole) and isopropanol (200 ml) at 26–28° C. After stirring overnight at room temperature, the mixture was poured into ice-water and acidified with dilute hydrochloric acid. The lower phase was separated and analyzed by gas chromatography. It was found that the mixture obtained was mainly the starting ester with some unidentified reaction products. The recovered product was added to a mixture of sodium borohydride 10.0 g (0.263 mole), isopropanol (200 ml) and diglyme (10 ml) at 45–50° C. After six hours, the reaction mixture was worked up as described above to give a product mixture consisting of at least six unidentified products and some unreacted starting ester but no noticeable amount of perfluoro-1H,1H-2-hexyldecanol.

EXAMPLE 2

Reduction of Perfluoro(Octyl Octanoate)

Perfluoro(octyl octanoate) (8967 g, 10.78 mole) (made by fluorination of the corresponding ester (octyl octanoate) was diluted with Halocarbon oil 0.8™ (an oligomer of chlorotrifluoroethylene) (Halocarbon Products Corp.) to 50 wt percent. The mixture was added dropwise to a mixture of sodium borohydride 657 g (17.2 mole) and diglyme (1 liter) in a stirred reactor. The reaction temperature was kept at 35° C. by external cooling and raised to 60° C. toward the end of the reaction time (about 4–5 hours). The mixture was cooled to room temperature and then about 4 kg of ice was added to the mixture. The cooled mixture was then carefully diluted with water (20 liters) with stirring, and the mixture was acidified with dilute hydrochloric acid. The lower organic phase was separated and washed twice with dilute hydrochloric acid. The lower organic phase was then fractionated to give perfluoro-1H,1H-octanol 7589 g (88% yield).

It can be seen that reduction of fluoralkyl ester of a straight-chain perfluorocarboxylic acid proceeds in good yield.

EXAMPLE 3

Reduction of Perfluoro(2-Hexyldexyl Acetate)

Perfluoro(2-hexyldecyl acetate) was prepared by the direct fluorination of the corresponding hydrocarbon according to a published procedure (Bierschenk et al. U.S. Pat. No. 5,093,432) in 70% yield. Perfluoro(2-hexyldecyl acetate) (3307 g, 3.55 mole) was diluted with Halocarbogn Oil 0.8™ (4 liters). The mixture was added to a mixture of sodium borohydride (202 g, 5.32 mole) and diglyme (100 ml) in a stirred reactor at 30–60° C. The reaction mixture was treated with ice-water as described above and acidified with dilute hydrochloric acid. The product was fractionated under vacuum to give 2200 g (77% yield) of perfluoro-1H,1H-2-hexyldecanol. Boiling point: 150° C./10 mmHg; Melting point: 73–75° C. The analytic data of this new compound are as follows: $^1$H NMR: —CH$_2$OH, 4.4 ppm; —CH$_2$OH, 5.3 ppm. $^{19}$F NMR: —CF$_3$, -81 ppm (6F); —CF$_2$—, -115 to -126 ppm (24F); —CF—, -191.5 ppm (1F). IR (cm$^{-1}$): 3311 (—OH); 1203, 1146 (C—F).

Thus, an α-branched perfluoroalkylmethanol was produced in good yield by reduction of a perfluoroalkyl ester of an α-branched perfluoroalkylcarboxylic acid.

EXAMPLE 4

Reduction of Perfluoro(Diethyl 2-octylmalonate)

Perfluoro(diethyl 2-octylmalonate) was prepared by the fluorination of the corresponding hydrocarbon in 65% yield. Perfluoro(diethyl 2-octylmalonate) (1632 g, 2.10 mole) diluted with Halocarbon Oil 0.8™ was added to a mixture of sodium borohydride 208 g (5.47 mole) and diglyme (500 ml) at 30–60° C. The reduction mixture was treated with ice-water and then acidified with dilute hydrochloric acid. The product mixture was fractionated under vacuum to give pure 2-fluoro-2-perfluorooctyl-1,3-propanediol 930 g (86% yield). Boiling point: 135° C./0.1 mmHg; Melting point: 145–149° C. The analytic data of this new compound are as follows: $^1$H NMR: —CH$_2$OH 4.09 ppm; —CH$_2$OH, 4.83 ppm. $^{19}$F NMR: —CF$_3$, -82.2 ppm (3F); —CF$_2$—, -120.3 to -127.2 ppm (14F); —CF—, -185.4 ppm (1F). IR (cm$^{-1}$): 3300 (—OH); 2900 (C—H); 1300–1100 (C—F).

EXAMPLE 5

Reduction of Perfluoro(Diethyl 2-Butylmalonate)

Diethyl 2-butylmalonate (497 g (2.3 mole) was fluorinated in Halocarbon Oil 0.8™. The fluorinated mixture was added to sodium borohydride 87 g (2.3 mole) suspended in stirred dimethoxyethane (3 liters). After reaction, The reduction mixture was carefully added to a diluted hydrochloric acid solution and the oily product layer was separated. The product mixture was fractionated under vacuum to give 2-fluoro-2-perfluorobutyl-1,3-propanediol. Boiling point: 80° C./0.1 mmHg.

The analytical data of this new compound are as follows: $^1$H NMR: —CH$_2$—, 4.18 ppm; —OH, 3.60 ppm. $^{19}$F NMR: —CF$_3$, -82.5 ppm (3F); —CF$_2$—, -121.8 to -127.8 ppm (6F); —CF—, -183.1 ppm (1F). IR (cm$^{-1}$): 3300 (—OH); 2900 (C—H); 1300–1100 (C—F).

EXAMPLE 6

Reduction of Perfluoro(Undecanoic τ-lactone)

Undecanoic τ-lactone 460 g (2.5 mole) was fluorinated in Halocarbon Oil 0.8™ (2 liter). The fluorinated mixture was then added to a solution containing sodium borohydride 95 g (2.5 mole) and dimethoxyethane (3 liter) at 33 to 45° C. After reaction, the reduction mixture was carefully poured into a solution of hydrochloric acid. The lower organic phase was separated and washed with dilute hydrochloric acid several times. Vacuum distillation gave 544 g of pure diol, perfluoro 1H,1H,4H-undecan-1,4-diol, CF$_3$(CF$_2$)$_6$—CH(OH)CF$_2$CF$_2$CH$_2$OH. Boiling point: 140° C./0.1 mmHg; Melting point: 75–78° C.

The analytical data of this new compound are as follows: $^1$H NMR: —CH$_2$—, 4.10 ppm; —CH, 4.78 ppm. $^{19}$F NMR: —CF$_3$, -82.0 ppm (3F); —CF$_2$—, -123.0 to -127.6 ppm (16F). IR (cm$^{-1}$): 3300 (—OH); 2900 (C—H); 1300–1100 (C—F).

EXAMPLE 7

Reduction of Perfluoro(Dodecanoic δ-lactone)

Dodecanoic δ-lactone 460 g (2.32 mole) was fluorinated in Halocarbon oil 0.8™ (6 liter). After most of the solvent was removed by distillation, the crude perfluoro(dodecanoic δ-lactone) mixture was added to a solution containing sodium borohydride 88 g (2.32 mole) and dimethoxyethane (2 liter) at 33 to 45° C. The reduction product was carefully hydrolyzed by pouring the reduction mixture into a solution of dilute hydrochloric acid. The lower organic phase was separated and washed several times with dilute hydrochloric acid. Vacuum distillation gave 300 g of pure diol, perfluoro 1H,1H,5H-dodecan-1,4-diol, CF$_3$(CF$_2$)$_6$—CH(OH)CF$_2$CF$_2$CF$_2$CH$_2$OH. Boiling point: 145° C./0.1 mmHg; Melting point: 88–91° C.

The analytical data of this new compound are as follows: $^1$H NMR: —CH$_2$—, 4.00 ppm; —CH, 4.80 ppm. $^{19}$F NMR: —CF$_3$, -82.0 ppm (3F); —CF$_2$—, -122.3 to -128.0 ppm (16F); . IR (cm$^{-1}$): 3300 (—OH); 2900 (C—H); 1300–1100 (C—F).

EXAMPLE 8

Surface Coating with Branched Perfluoralkyl Methanol Polymers

The compound produced in Example 4, supra, can be employed to provide a durable, low-friction surface coating. The compound, perfluoro-1H,1H-(2-hexyldecanol), is converted to the acrylate ester by treatment with acryloyl chloride in the presence of a suitable tertiary amine base, such as triethylamine. The perfluoro-1H,1H-(2-hexyldecanol) acrylate is then coated onto a surface, such as a primed metal surface, and the acrylate moieties are polymerized, e.g., with a radical initiator or UV radiation, to provide a durable surface coating of an acrylic polymer substituted with branched-chain perfluoroalkyl chains along the backbone.

Those skilled in the art will recognize, or be able to ascertain using no more than routine experimentation, many equivalents to the specific embodiments of the invention described herein. Such equivalents are intended to be encompassed by the following claims. The contents of all publications and patents cited herein are hereby incorporated by reference.

I claim:

1. A compound selected from the group consisting of perfluoro-1H,1H-2-hexyldecanol, 2-fluoro-2-perfluorooctyl-1,3-propanediol, 2-fluoro-2perfluorobutyl-1,3-propanediol, perfluoro 1H,1H,4H-undecane 1,4-diol, and perfluoro 1H,1H,5H-dodecane-1,5-diol.

2. A perfluoro 1H,1H,nH-alkyl-1,n-diol, in which the alkyl moiety includes from 3 to 15 carbon atoms, and n is an integer from 3 to 15.

3. A perfluoroalkyl methanol compound represented by the formula $HOCH(R_f)$—$R'_f$—$CH_2OH$, wherein $R'_f$ is a perfluorocarbon moiety and $R_f$ is a perfluorocarbon moiety, wherein $R'_f$ and $R_f$ may be independently substituted by a halogen, hydroxyl, alkyl, alkoxyl, cyano, azido, heterocyclyl, aralkyl, aromatic, or heteroaromatic moiety, or perfluorinated derivatives thereof.

4. The compound of claim 3, wherein $R'_f$ is a divalent, perfluorinated, alkyl or alkenyl organic radical having one to twenty carbon atoms, wherein the radical can be interrupted by divalent oxygen or sulfur atoms and may be substituted by a halogen, hydroxyl, alkyl, alkoxyl, cyano, azido, heterocyclyl, aralkyl, aromatic, or heteroaromatic moiety, or perfluorinated derivatives thereof.

5. The compound of claim 3, wherein $R_f$ is a perfluoroalkyl moiety, wherein $R_f$ may be substituted by a halogen, hydroxyl, alkyl, alkoxyl, cyano, azido, heterocyclyl, aralkyl, aromatic, or heteroaromatic moiety, or perfluorinated derivatives thereof.

6. The compound of claim 3, wherein $R'_f$ and $R_f$ are selected from the group consisting of trifluoromethyl, pentafluoroethyl, heptafluoroisopropyl, 2-trifluoromethoxy perfluoropentyl, perfluorocyclopentyl, wherein $R'_f$ and $R_f$ may be independently substituted by a halogen, hydroxyl, alkyl, alkoxyl, cyano, azido, heterocyclyl, aralkyl, aromatic, or heteroaromatic moiety, or perfluorinated derivatives thereof.

7. A perfluoroalkyl methanol compound represented by the formula $HOCH(R_f)$—$R'_f$—$CH_2OH$, wherein $R'_f$ is a perfluoroalkyl moiety and $R_f$ is perfluoroalkyl moiety, wherein $R'_f$ and $R_f$ may be independently substituted by a halogen, hydroxyl, alkyl, alkoxyl, cyano, azido, heterocyclyl, aralkyl, aromatic, or heteroaromatic moiety, or perfluorinated derivatives thereof.

8. The compound of claim 7, wherein $R'_f$ is a divalent, perfluorinated, alkyl or alkenyl organic radical having one to twenty carbon atoms, wherein the radical can be interrupted by divalent oxygen or sulfur atoms and may be substituted by a halogen, hydroxyl, alkyl, alkoxyl, cyano, azido, heterocyclyl, aralkyl, aromatic, or heteroaromatic moiety, or perfluorinated derivatives thereof.

9. The compound of claim 7, wherein $R_f$ is a perfluoroalkyl moiety, wherein $R_f$ may be substituted by a halogen, hydroxyl, alkyl, alkoxyl, cyano, azido, heterocyclyl, aralkyl, aromatic, or heteroaromatic moiety, or perfluorinated derivatives thereof.

10. The compound of claim 7, wherein $R'_f$ and $R_f$ are selected from the group consisting of trifluoromethyl, pentafluoroethyl, heptafluoroisopropyl, 2-trifluoromethoxy perfluoropentyl, perfluorocyclopentyl, wherein $R'_f$ and $R_f$ may be independently substituted by a halogen, hydroxyl, alkyl, alkoxyl, cyano, azido, heterocyclyl, aralkyl, aromatic, or heteroaromatic moiety, or perfluorinated derivatives thereof.

* * * * *